Figure 1:
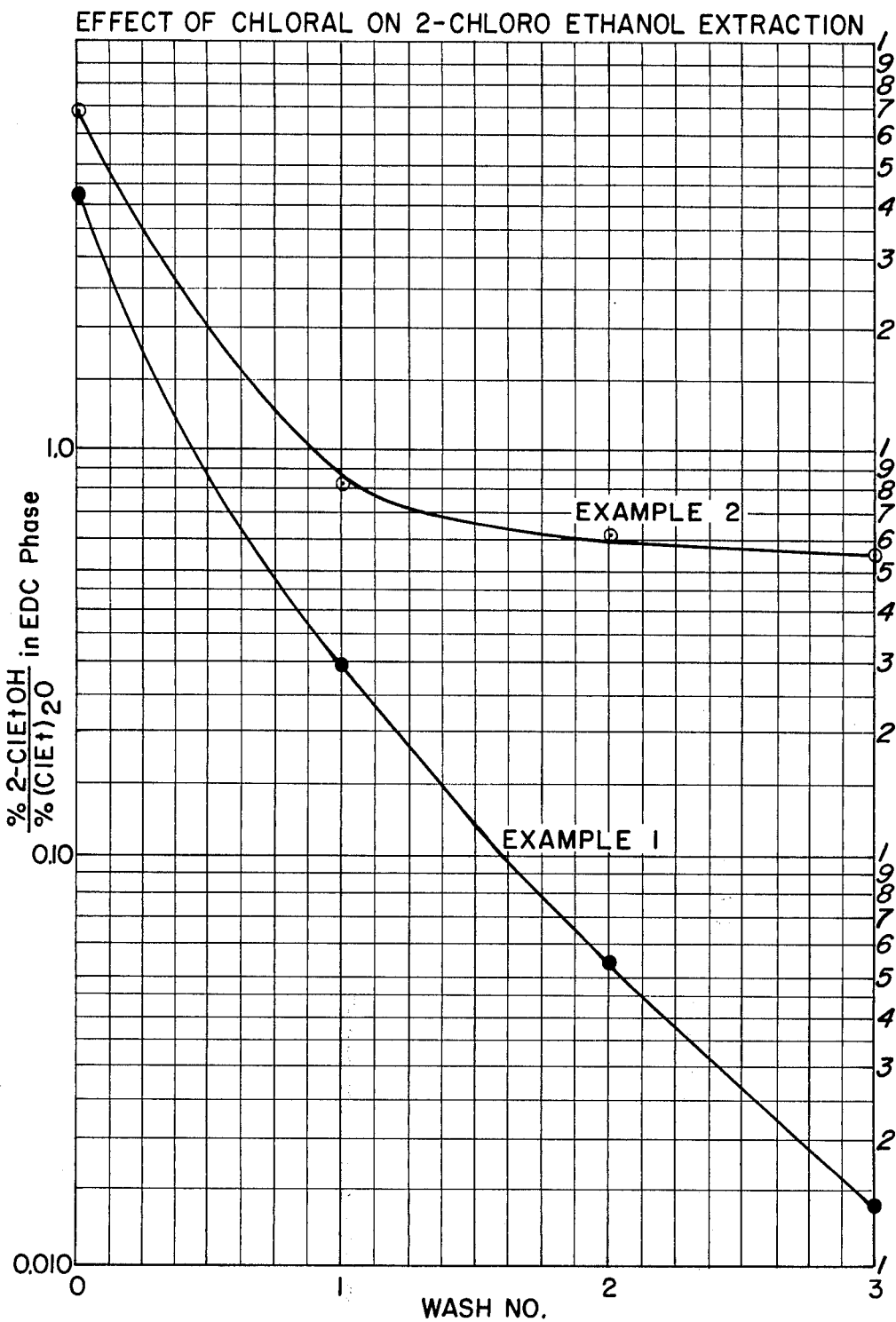

United States Patent [19]

Convers

[11] 4,141,922
[45] Feb. 27, 1979

[54] PROCESS FOR PURIFICATION OF 1,2-DICHLOROETHANE

[75] Inventor: Ronald J. Convers, Ponca City, Okla.

[73] Assignee: Continental Oil Company, Ponca City, Okla.

[21] Appl. No.: 879,335

[22] Filed: Feb. 21, 1978

[51] Int. Cl.² ............................................. C07C 17/38
[52] U.S. Cl. .............................. 260/652 P; 568/841; 568/867
[58] Field of Search .................................... 260/652 P

[56] References Cited

U.S. PATENT DOCUMENTS

| | | | |
|---|---|---|---|
| 3,996,300 | 12/1976 | Ahlstrom | 260/652 P |
| 3,998,706 | 12/1976 | Fruhwith et al. | 260/652 P |

*Primary Examiner*—C. Davis
*Attorney, Agent, or Firm*—Cortlan R. Schupbach, Jr.

[57] ABSTRACT

A method is provided for the removal of 2-chloroethanol from 1,2-dichloroethane (EDC) mixtures containing chloral comprising
 (1) placing the EDC/2-chloroethanol mixture at a pH of at least 10,
 (2) partially distilling said basic mixture to remove ethylene oxide from the resulting mixture of (1),
 (3) mixing the distillate with water in contact with a strong non-halogen acid catalyst to form an aqueous and organic phase, and
 (4) recovering the reaction product of (3) while separating and disposing the aqueous phase.

3 Claims, 1 Drawing Figure

PROCESS FOR PURIFICATION OF 1,2-DICHLOROETHANE

This invention deals with a method for the disposal of 2-chloroethanol by conversion to readily biodegradable ethylene glycol. More particularly, this invention deals with a method for the disposal of 2-chloroethanol from industrial 1,2-dichloroethane (EDC) solution into a readily biodegradable environmentally acceptable form such as ethylene glycol.

During the production of 1,2-dichloroethane (EDC) by chlorination of ethylene in the presence of water, 2-chloroethanol is formed as a by-product. While 2-chloroethanol is only a minor by-product of commercial ethylene oxychlorination processes, this material is very troublesome to plant operations for several reasons. The by-product 2-chloroethanol is water soluble and toxic at low concentrations to conventional plant biopond micro-organisms which purify effluent streams. Plant effluents with excessive oxygen demand and particulant matter can thus result from 2-chloroethanol production, since biopond micro-organisms are destroyed by contact with 2-chloroethanol. The 2-chloroethanol is a precursor to oxygenates such as ethylene oxide (EO), and acetaldehyde produced from base treatment or thermal cracking. These oxygenates presently decrease the market value of the low boiling by-product chlorohydrocarbon streams known in the industry as EDC light ends. In addition, 2-chloroethanol is believed to be responsible for corrosion of steel and distillation towers used to recover EDC light ends because of thermal cracking to hydrochloric acid and ethylene oxide and acetaldehyde. Further, 2-chloroethanol is believed to cause excessive tar formation during production of vinyl chloride by the thermal cracking of EDC.

Thus it is very apparent that it is desirable to remove 2-chloroethanol from commercial ethylene oxychlorination product streams. Commercial plants presently depend either on an extra fractionation of EDC distillation bottoms which is relatively expensive in equipment, energy, and ultimate disposal costs or on aqueous sodium hydroxide washes of crude EDC to convert 2-chloroethanol to less troublesome derivatives such as ethylene oxide or ethylene glycol.

However, during attempts to convert 2-chloroethanol to ethylene oxide followed by the hydrolysis of ethylene oxide to ethylene glycol in conventional plant systems, it was found that 2-chloroethanol is ultimately not removed completely, but instead continues to pass to a biopond where its harmful effects previously described continue to be felt.

The reaction to form ethylene oxide is rapid even in the usual two-phase wash system commonly used in commercial facilities in the present art. However, the sodium hydroxide conversion of 2-chloroethanol to the desirable ethylene glycol is so slow as to be commercially impractical using conventional two-phase wash systems. In addition, the ethylene oxide reconverts to 2-chloroethanol in the presence of hydrochloric acid, traces of which are found in later parts of the EDC purification train.

It is known in the art that ethylene oxide can be hydrolyzed to form ethylene glycol and that 2-chloroethanol can be converted to ethylene oxide. While such references are too numerous to mention, representative examples can be found in U.S. Pat. No. 2,839,588; U.S. Pat. No. 2,742,505; Stanford Research Institute Reports No. 70 and 70A; *Journal of American Chemical Society*, Volume 80, pages 4162–4165; *Petroleum Refiner*, Volume 28, No. &, 1949, pages 120–124; and *Hydrocarbon Processing*, Volume 46, issue 4, pages 176–178, 1967. Additionally, in the previous patent application of which I am co-inventor, Serial No. 804,113, filed June 6, 1977, now U.S. Patent No. 4,087,474, an alternate method for the purification of 1,2-dichloroethane from 2-chloroethanol was discovered and described. However, that method carried out all operations on the water phase of the process which was basified, steam stripped, and disposed. However, it has been found that a multi-stage water extractor is required for efficient use of the process described patent application Serial No. 804,113 to remove all 2-chloroethanol from crude EDC.

It would be greatly desirable to devise a process whereby 2-chloroethanol could be ecomically, quickly, and completely removed from crude EDC streams and converted into relatively harmless ethylene glycol for biopond disposal without the necessity for multi-stage extractions.

It is therefore an object of the present invention to provide a method for the removal of 2-chloroethanol from commercial EDC streams by the formation of ethylene glycol which is readily biodegradable and which can be carried out in a single process. Other objects will become apparent to those skilled in this art as the description proceeds.

It has now been discovered according to the instant invention that the partition coefficient for 2-chloroethanol in EDC and water unexpectedly increases considerably when chloral is present in the EDC in concentrations equal to or greater than that of the 2-chloroethanol present. The presence of chloral means that a water extraction based on EDC purification system such as described in our previously filed application 804,113 necessarily becomes less efficient and more costly in terms of equipment needed as chloral concentration increases.

A method has been devised to avoid the multi-stage extraction necessary in the best available prior art. As in the prior art processes, the invention is carried out in steps yet does not require multi-stage extraction.

The first step of the present invention is partial distillation of the EDC stream containing 2-chloroethanol and chloral from a stirred vessel maintained at a pH of 10 or higher with aqueous sodium hydroxide or other metal hydroxide. The partial distillation is carried out to remove ethylene oxide from both the major part of the EDC, that is to both concentrate the ethylene oxide for subsequent conversion to ethylene glycol and to save on energy and equipment costs involved in total distillation of the based treated EDC and to also remove a concurrently generated sodium chloride. This step was shown to be critically necessary in copending Ser. No. 804,113. The distillation bottoms from this step, now free of 2-chloroethanol, are suitable for injection into the usual plant base wash separator and the overhead fraction which contains ethylene oxide is mixed with warm water in the presence of a strong acid catalyst in an air tight system to convert the ethylene oxide to ethylene glycol. The strong acid catalyst should be acid other than hydrohalogens, preferably sulfuric acid or sulfonic acid ion exchange resins. Such catalysts have been amply described in ethylene oxide hydration literature.

The total overhead liquid stream is then suitable as feed for the usual plant steam stripper. The ethylene glycol leaves the chemical treatment system in the steam stripper bottoms and is ready for biodegradation in the usual plant bioponds. Thus the present invention provides a relatively inexpensive process for the removal of toxic 2-chloroethanol from ethylene oxychlorination streams with minimal consequential water pollution. The base conversion reaction and ethylene oxide hydration are long-known reactions but their combined use in this water pollutionABATEMENT process is useful and entirely unpredictable on the basis of the criticality of the ethylene oxide distillation requirement which is set forth in our previously filed application 804,113 and the effect the chloral concentration has on water extraction based on EDC purification systems.

Concisely described, therefore, the instant invention is a method for the removal of 2-chloroethanol from 1,2-dichloroethane (EDC) mixtures containing chloral comprising;

(1) placing the EDC/2-chloroethanol mixture at a pH of at least 10,
(2) partially distilling said basic mixture to remove ethylene oxide from the resulting mixture of (1),
(3) mixing the distillate with water in contact with a strong, non-halogen acid catalyst to form an aqueous or organic phase thereby converting ethylene oxide to water soluble ethylene glycol, and
(4) recovering the reaction product of (3) while separating and disposing the aqueous phase.

As set forth above, the base used to maintain the pH of about 10 is preferably any metal hydroxide base such as sodium hydroxide, potassium hydroxide, barium hydroxide, lithium hydroxide, and calcium hydroxide. The strong non-halogen acid catalyst can be any one of several well-known in the art. Representative examples of such acids are sulfuric, sulfonic acid ion exchange resins, silica alumina catalysts, etc. It is emphasized that any non-halogen acid known to convert ethylene oxide to ethylene glycol can be used.

The invention is more concretely described with reference to the examples below wherein all parts and percentages are by weight unless otherwise specified. The examples are provided to illustrate the present invention and not to limit it.

Products were sampled as liquid and analyzed by gas liquid chromatography (GLC model 1200 Varian Aerograph) using flame ionization detector and computer integration. The GLC used had about 10 foot by 1/8 inch stainless steel column containing 7.6 weight percent free fatty acid phase (polyethylene glycol of about 20,000 molecular weight, capped with dinitroterphthalic acid on a 100–115 mesh support).

Example 1 shows that, in the absence of chloral, 2-chloroethanol is readily extracted by water from EDC to afford a simple, easily base-treatable, 2-chloroethanol-containing phase.

Example 2 shows that chloral drastically effects the efficiency of 2-chloroethanol extraction by water from EDC.

An examination of FIG. 1 graphically illustrates on a log-log scale the effect of chloral on 2-chloroethanol extractions. The graph dramatically demonstrates that in the absence of chloral, a single wash will accomplish more 2-chloroethanol extraction than several washes when chloral is present.

Example 3 shows that the base conversion of 2-chloroethanol to ethylene oxide is rapid, even in the 2 phase system used, and that the resultant ethylene oxide can be removed from the EDC by distilling a relatively small part of the reaction mixture.

Example 4 shows that ethylene oxide in the distillate from Example 3 can be expected to hydrolyze readily in acidic conditions.

Example 5 shows that the 2-phase base hydrolysis of ethylene oxide is slow.

EXAMPLE 1

A solution of 1.5 grams of 2-chloroethanol, .5 grams of bis-2-chloroethyl ether, and 98 grams of EDC was extracted 3 times with equal weights of distilled water (1:1 weight ratio of EDC:water). The 2-chloroethanol concentrations in the EDC phases were compared to that of the starting solution by gas liquid chromatography. Bis-2-chloroethyl ether was used as an internal GLC standard, since it is not extractable in detectable amounts under the conditions used. FIG. 1 shows a plot of the GLC area percent ratio of 2-chloroethanol/bis-2-chloroethyl ether vs the number of water washes.

EXAMPLE 2

A solution of 1.5 grams of 2-chloroethanol, 0.5 grams of bis-2-chloral ethyl ether, 3 grams of chloral hydrate and 92 grams of EDC was extracted three times with equal weights of water (1:1 weight to weight EDC to water). FIG. 1 shows the plot of area percent ratio of 2-chloroethanol/bis-2-chloral ethyl ether vs the number of water washes. It is apparent that the rate of removal of 2-chloroethanol from EDC is greatly reduced by the presence of the chloral.

EXAMPLE 3

A mixture of 275 grams of 12% aqueous sodium hydroxide and 723 grams of crude acidic EDC containing 1.6 weight percent of 2-chloroethanol and 2 weight percent chloral (calculated as the hydrate) was magnetically stirred in a 1 liter round bottom flask and partially distilled through a Claisen still head fitted with an ice water condenser into dry ice cooled receivers. GLC examination of the flask contents essentially showed no 2-chloroethanol present after 2½ minutes at 38°–46°C., and no ethylene oxide present after distillation of about 110 grams of material. The flask temperature was about 60° C.

EXAMPLE 4

A mixture of 1.9 grams of water, .23 grams of 98% sulfuric acid, and 7.64 grams of 1 weight percent solution of ethylene oxide in EDC was shaken for 2 minutes at about 50° C in a capped 2 ounce glass bottle. Gas liquid chromatography then showed no ethylene oxide remaining and less than .01 weight percent of 2-chloroethanol in the EDC phase. The starting 1.0 weight percent ethylene oxide solution showed .06 weight percent of 2-chloroethanol present by GLC. About 70% of this original 2-chloroethanol was finally observable in the aqueous phase.

EXAMPLE 5

A mixture of 2 grams of 1 weight percent aqueous sodium hydroxide and 7.64 grams of a 1 weight percent solution of ethylene oxide in EDC was shaken for about 3 minutes at ambient temperature in a capped 2 ounce bottle. Gas liquid chromatography showed 3.7 area percent of ethylene oxide remaining. The mixture was shaken for 2 minutes at about 50°C., and GLC showed 1.4 area percent of ethylene oxide remaining. The mixture was left capped at ambient temmperature for 1 hour and then shaken for an additional 2 minutes at about 50° C. GLC showed about .04 area percent of ethylene oxide remaining at the end of the test.

This it is apparent that example 1 shows in the absence of chloral that only 1 or 2 water washes is capable of removing 2-chloroethanol. Example 2 shows that in the presence of chloral the partition coefficient is raised to such a level that the efficiency of the water extraction is greatly reduced. Example 3 is a demonstration of the use of base in the conversion of 2-chloroethanol to ethylene oxide.

An examination of the present invention in comparison to the prior art will show that the present invention has provided a method for the removal of 2-chloroethanol from commercial EDC streams primarily as the ethylene oxide derivative as compared to concentrating the troublesome material into a relatively strong aqueous stream, and converting the 2-chloroethanol by basifying, steam stripping and hydrolyzing where several water extractions are required. The instant invention provides for a single treatment of the entire EDC stream containing both aqueous and organic phases in a simple treatment. The instant invention has realized the effect of chloral upon the water partition coefficient which made extraction extremely inefficient and required several extractions to reduce 2-chloroethanol to acceptable levels. The invention thus avoids the problems found in the prior art which required many extractions and still reduces 2-chloroethanol going to bioponds to acceptable levels by converting the 2-chloroethanol to ethylene oxide which is hydrolyzed to ethylene glycol which is then readily biodegradable.

While certain embodiments and details have been shown for the purpose of illustrating this invention, it will be apparent to those skilled in this art that various changes and modifications may be made herein without departing from the spirit or the scope of the invention.

I claim:

1. A method for the removal of 2-chloroethanol from 1,2-dichloroethane (EDC) mixtures containing chloral comprising:
   (1) placing the 1,2-dichloroethane/2-chloroethanol mixture at a pH of at least 10,
   (2) partially distilling said basic mixture to remove ethylene oxide from the resulting mixture of 1,
   (3) mixing the distillate with water in contact with a strong non-halogen acid catalyst to form an aqueous phase and an organic phase, thereby converting ethylene oxide to water soluble ethylene glycol, and
   (4) recovering 1,2-dichloroethane as the organic phase of
   (3) while separating and disposing the aqueous phase containing ethylene glycol.

2. A method as described in claim 1 wherein the base used is a metal hydroxide base selected from the group consisting of sodium hydroxide, barium hydroxide, potassium hydroxide, lithium hydroxide, and calcium hydroxide.

3. A method as described in claim 2 wherein the acid catalyst is selected from the group consisting of sulfuric acid, sulfonic acid ion exchange resin, and silica alumina.

* * * * *